(12) United States Patent
Gerstel

(10) Patent No.: US 10,520,519 B2
(45) Date of Patent: Dec. 31, 2019

(54) ARRANGEMENT FOR PREPARING A PLURALITY OF SAMPLES FOR AN ANALYTICAL METHOD

(71) Applicant: Joachim Gerstel, Mulheim a.d. Ruhr (DE)

(72) Inventor: Joachim Gerstel, Mulheim a.d. Ruhr (DE)

( * ) Notice: Subject to any disclaimer, the term of this patent is extended or adjusted under 35 U.S.C. 154(b) by 108 days.

(21) Appl. No.: 15/329,866

(22) PCT Filed: Jul. 24, 2015

(86) PCT No.: PCT/EP2015/066965
§ 371 (c)(1),
(2) Date: Jan. 27, 2017

(87) PCT Pub. No.: WO2016/016109
PCT Pub. Date: Feb. 4, 2016

(65) Prior Publication Data
US 2017/0269112 A1    Sep. 21, 2017

(30) Foreign Application Priority Data

Jul. 29, 2014    (DE) .................. 10 2014 110 680
Jul. 29, 2014    (DE) .................. 10 2014 110 682
(Continued)

(51) Int. Cl.
*G01N 35/02* (2006.01)
*B04B 11/04* (2006.01)
(Continued)

(52) U.S. Cl.
CPC ........... *G01N 35/025* (2013.01); *B01D 35/02* (2013.01); *B01F 5/0057* (2013.01);
(Continued)

(58) Field of Classification Search
None
See application file for complete search history.

(56) References Cited

U.S. PATENT DOCUMENTS 3,596,673 A    8/1971    Laucournet
5,604,130 A    2/1997    Warner et al.
(Continued)

FOREIGN PATENT DOCUMENTS

CN    1148892 A         4/1997
DE    202011110050 U1   1/2013
WO    WO 2009/068749 A2 6/2009

OTHER PUBLICATIONS

PCT Application No. PCT/EP2015/066965; Filing Date Mar. 3, 2016, Joachim Gerstel, International Search Report, dated Nov. 3, 2016. 3 Pages.

*Primary Examiner* — Kathryn Wright
(74) *Attorney, Agent, or Firm* — Thorpe North and Western, LLP

(57) ABSTRACT

The invention relates to an arrangement for preparing a plurality of samples for an analytical method, comprising a carousel with a solid housing and moveable receiving parts for the sample containers; a control for controlling the receiving parts in the carousel; and a sample receiving device for providing the sample for the analytical method. Said arrangement is characterized in that one or more stations for preparing samples are provided on the carousel, the receiving parts for the sample containers of the carousel can be positioned on said stations. Said arrangement also comprises a centrifuge with pairs of opposite lying receiving parts provided for the sample containers, and said receiving parts are arranged such that they can move on the centrifuge for the sample holder such that a transfer of a sample holder between a receiving part in the carousel and a receiving part in the centrifuge can be carried out. The control takes place (Continued)

by the same control which is also provided for controlling the carousel.

19 Claims, 16 Drawing Sheets

(30) Foreign Application Priority Data

Jul. 29, 2014 (DE) .................. 10 2014 110 684
Jul. 29, 2014 (DE) .................. 10 2014 110 691

(51) Int. Cl.
| | | |
|---|---|---|
| *B04B 5/10* | (2006.01) | |
| *B04B 5/04* | (2006.01) | |
| *G01N 35/10* | (2006.01) | |
| *B01D 35/02* | (2006.01) | |
| *B01F 5/00* | (2006.01) | |
| *B01L 3/02* | (2006.01) | |
| *G01N 1/28* | (2006.01) | |
| *G01N 35/00* | (2006.01) | |
| *G01N 35/04* | (2006.01) | |

(52) U.S. Cl.
CPC .......... *B01L 3/0275* (2013.01); *B04B 5/0414* (2013.01); *B04B 5/0421* (2013.01); *B04B 11/043* (2013.01); *G01N 1/286* (2013.01); *G01N 35/00732* (2013.01); *G01N 35/04* (2013.01); *G01N 35/10* (2013.01); *G01N 35/1011* (2013.01); *G01N 35/1079* (2013.01); *B01F 2215/0037* (2013.01); *B01L 2300/0681* (2013.01); *B04B 2011/046* (2013.01); *G01N 35/1097* (2013.01); *G01N 2001/2873* (2013.01); *G01N 2035/0405* (2013.01); *G01N 2035/0449* (2013.01); *G01N 2035/103* (2013.01); *G01N 2035/1025* (2013.01); *G01N 2035/1053* (2013.01)

(56) References Cited

U.S. PATENT DOCUMENTS

| | | |
|---|---|---|
| 5,863,754 A | 1/1999 | Bajard |
| 6,027,694 A | 2/2000 | Boulton et al. |
| 7,745,204 B1 | 6/2010 | Aidun et al. |
| 9,383,377 B2 | 7/2016 | Loppacher et al. |
| 2002/0123156 A1 | 9/2002 | Tajima |
| 2003/0039589 A1 | 2/2003 | Smith |
| 2005/0016916 A1 | 1/2005 | Zermani |
| 2007/0134131 A1 | 6/2007 | Watson et al. |
| 2009/0294385 A1 | 12/2009 | Tajima et al. |
| 2011/0107855 A1 | 5/2011 | Motadel |
| 2012/0105837 A1 | 5/2012 | Ingber |
| 2012/0244541 A1 | 9/2012 | Rapp |
| 2013/0128035 A1 | 5/2013 | Johns et al. |
| 2013/0327195 A1 | 12/2013 | Routamaa et al. |

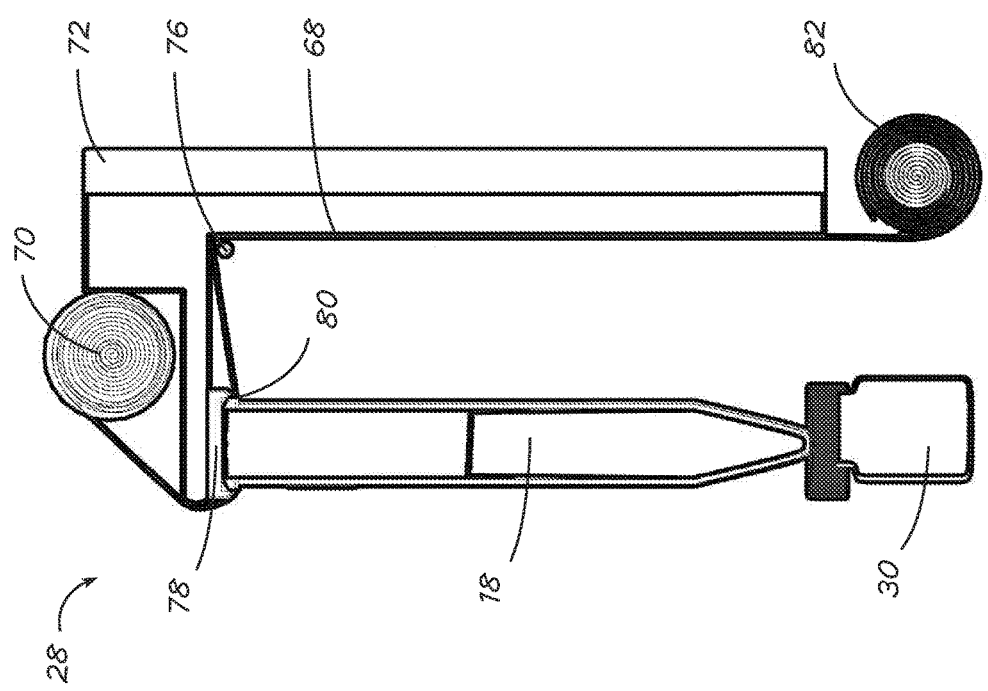
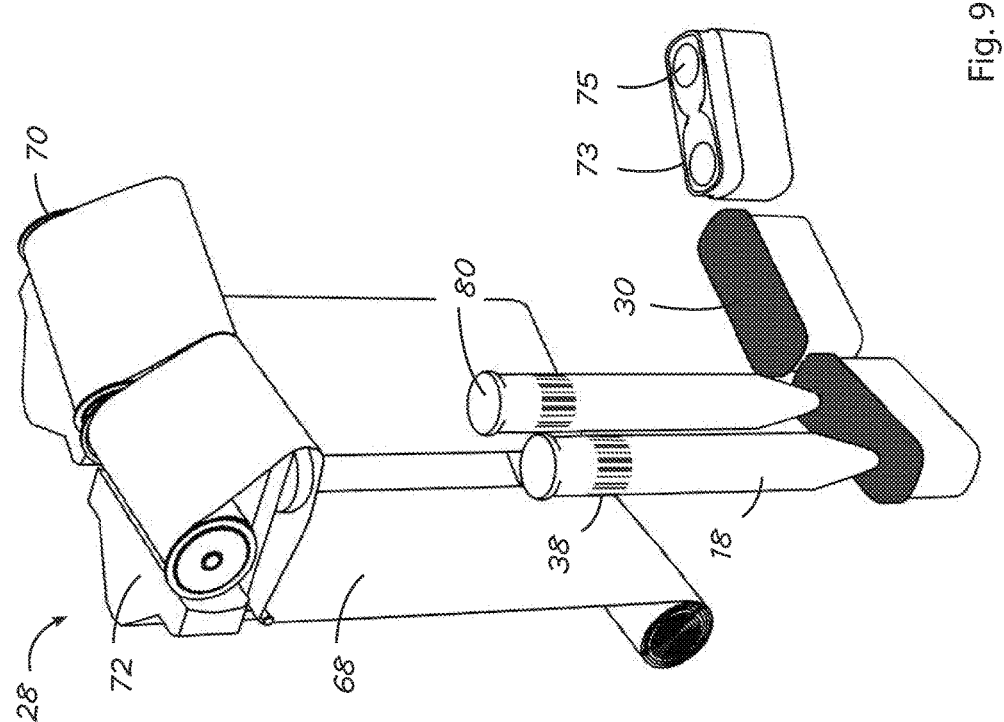
Fig. 10
Fig. 9

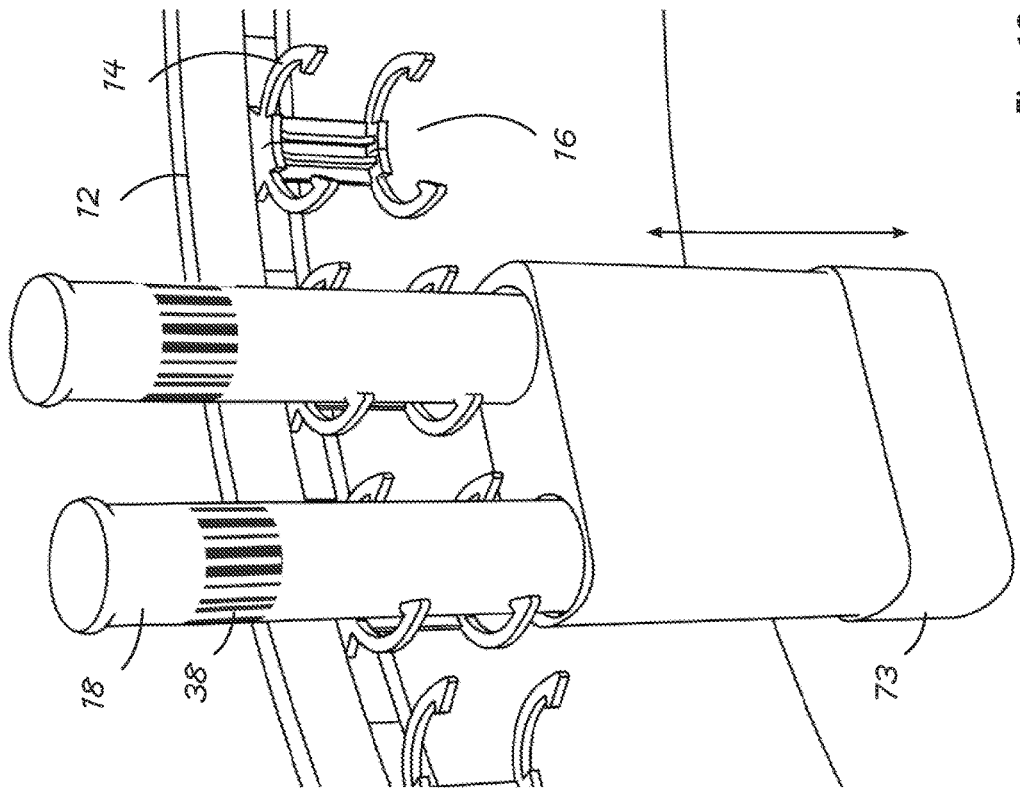
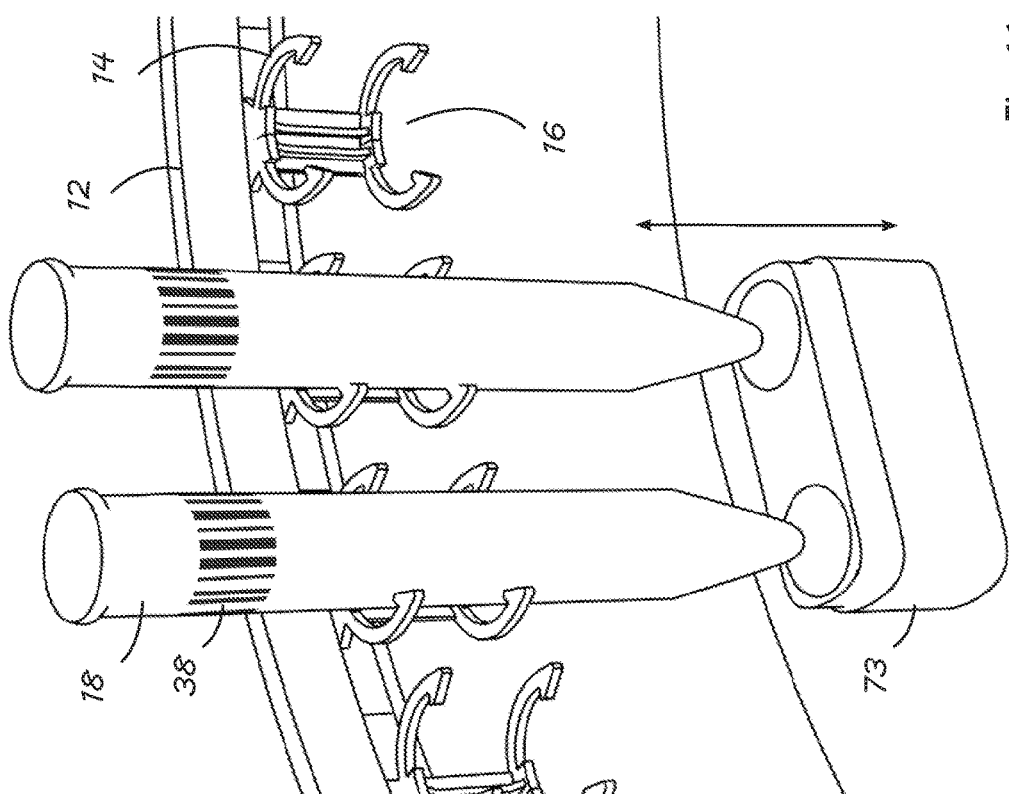

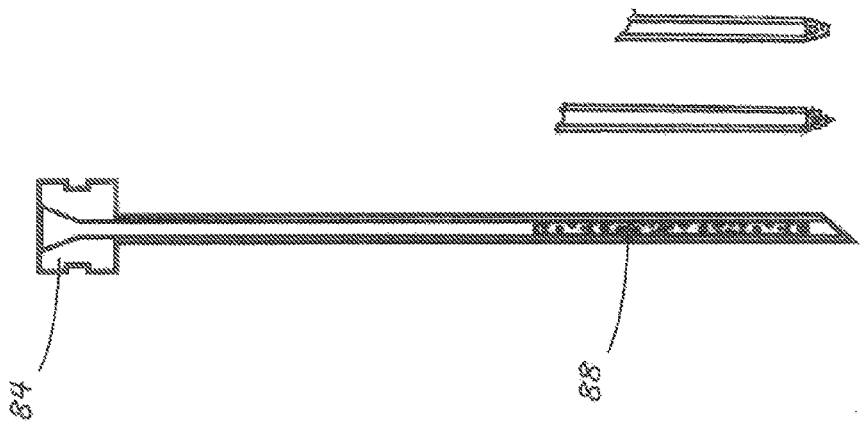
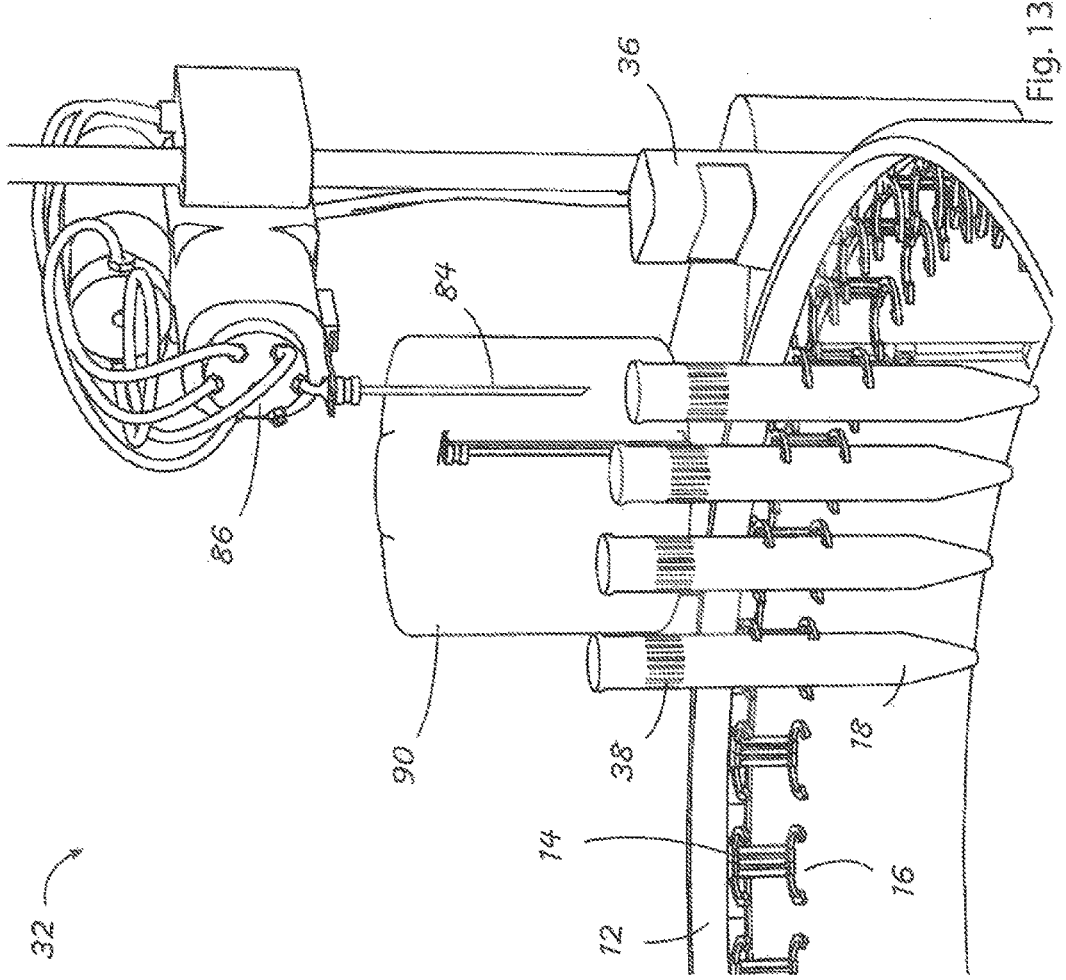

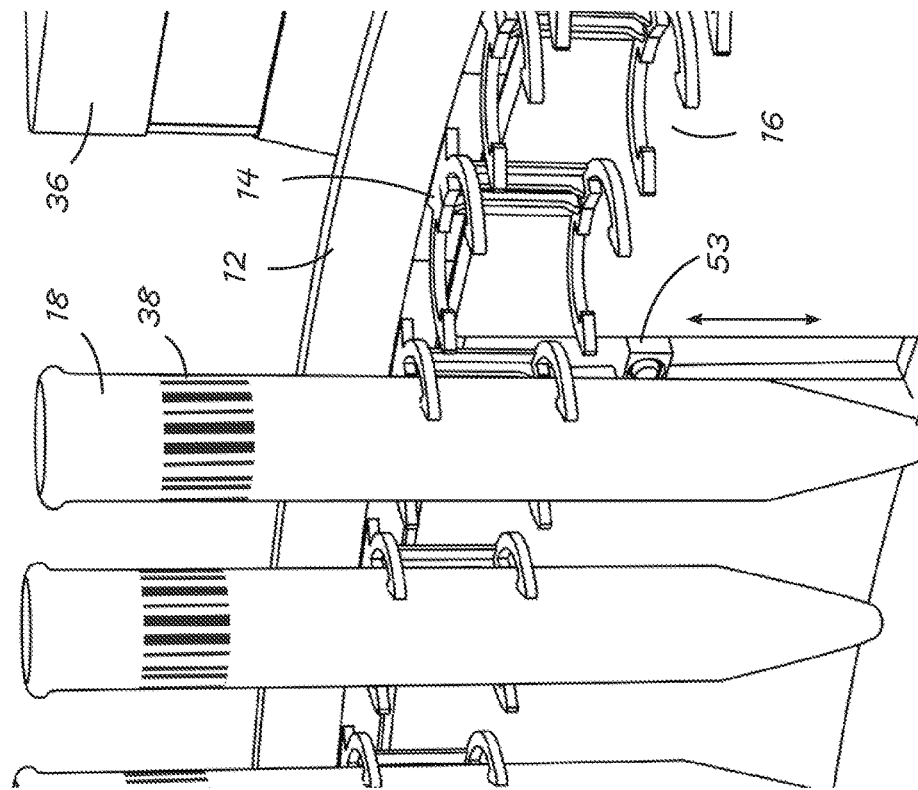
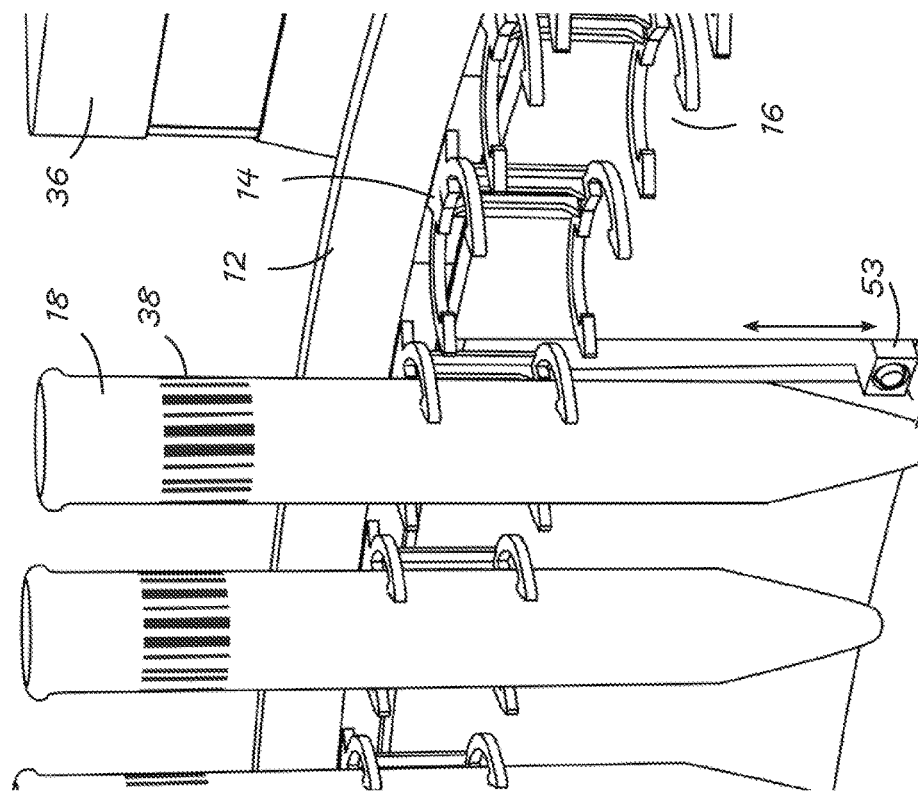

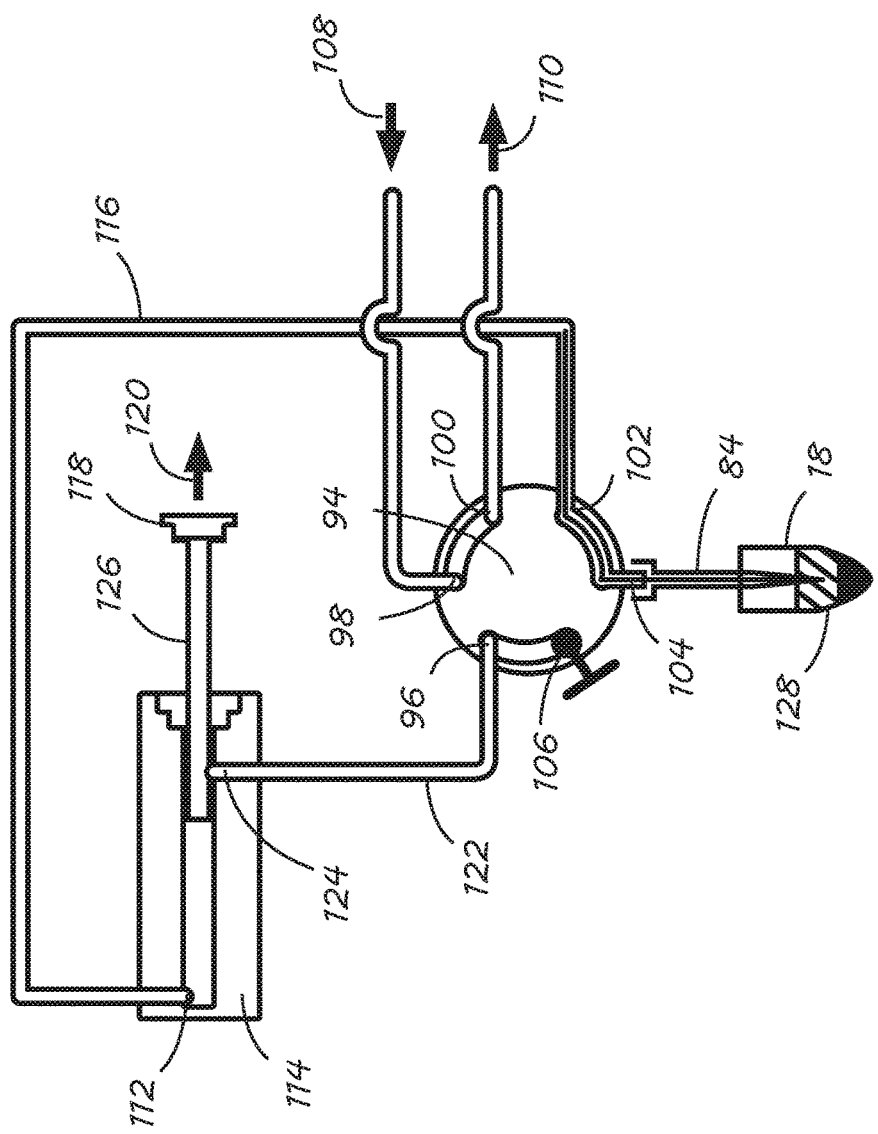

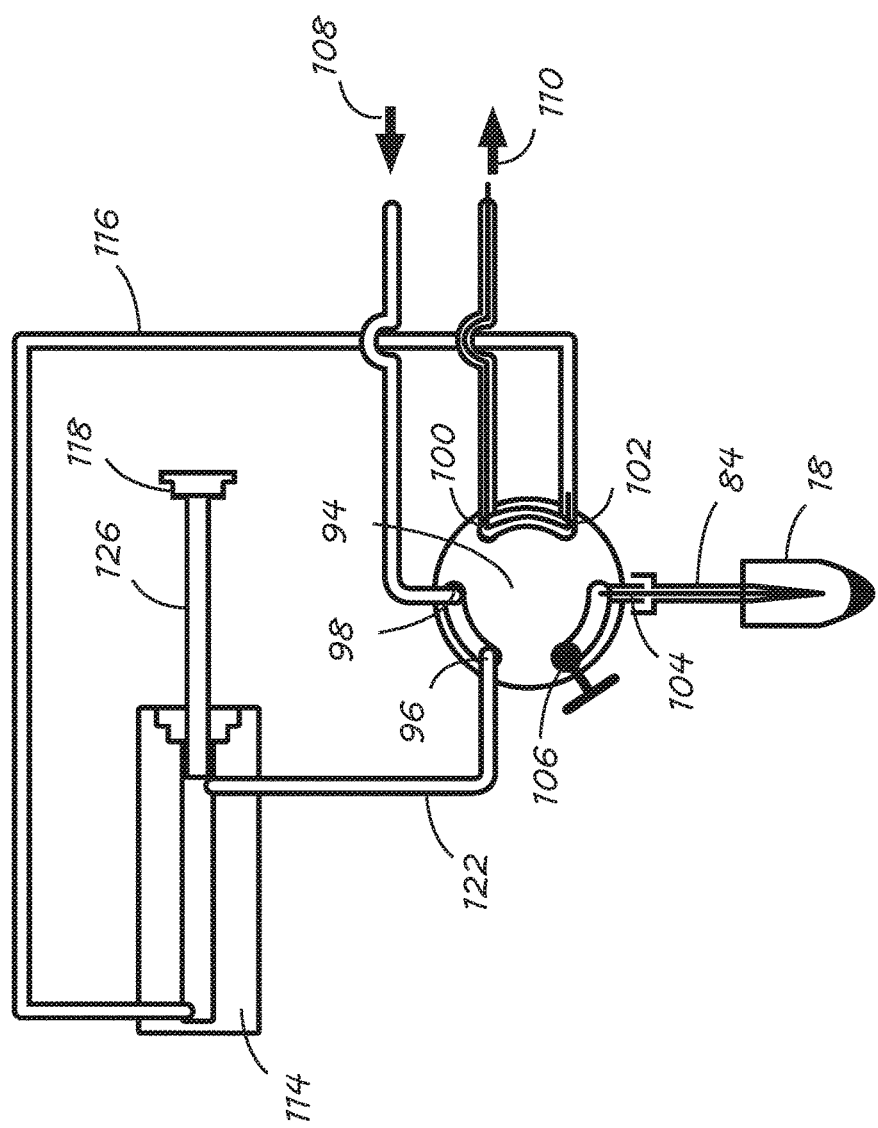

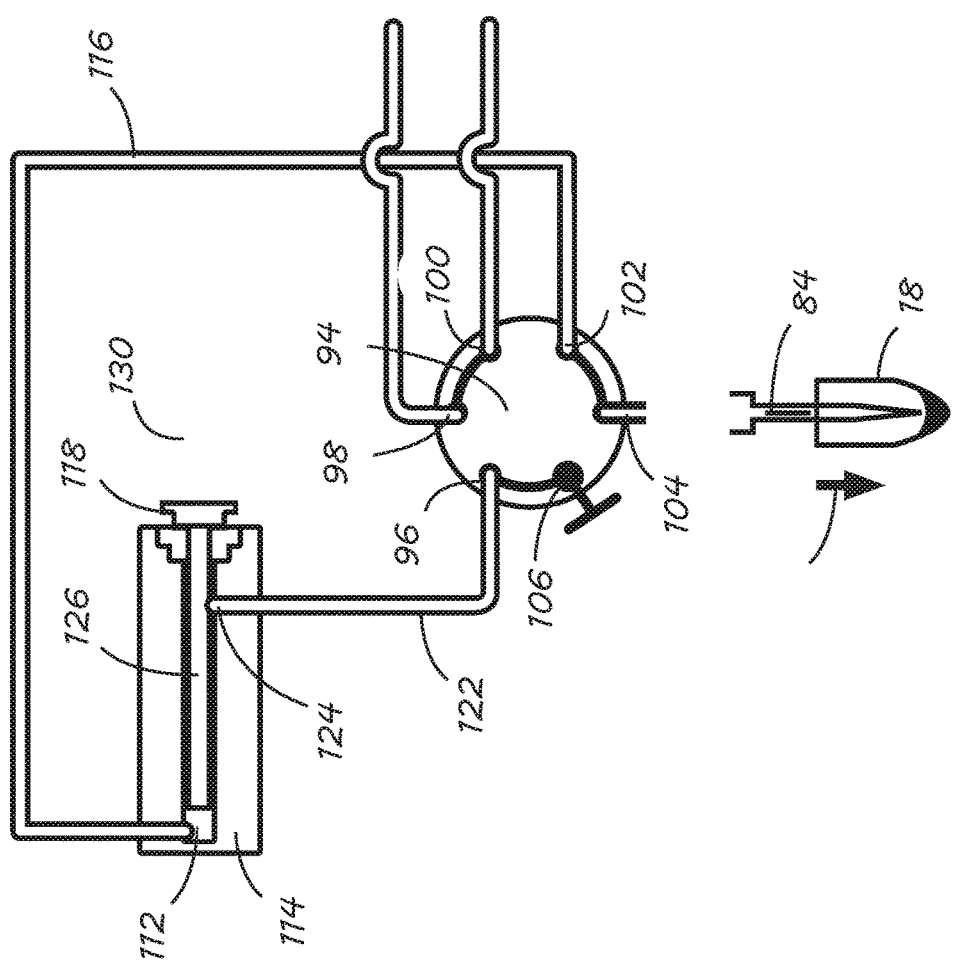

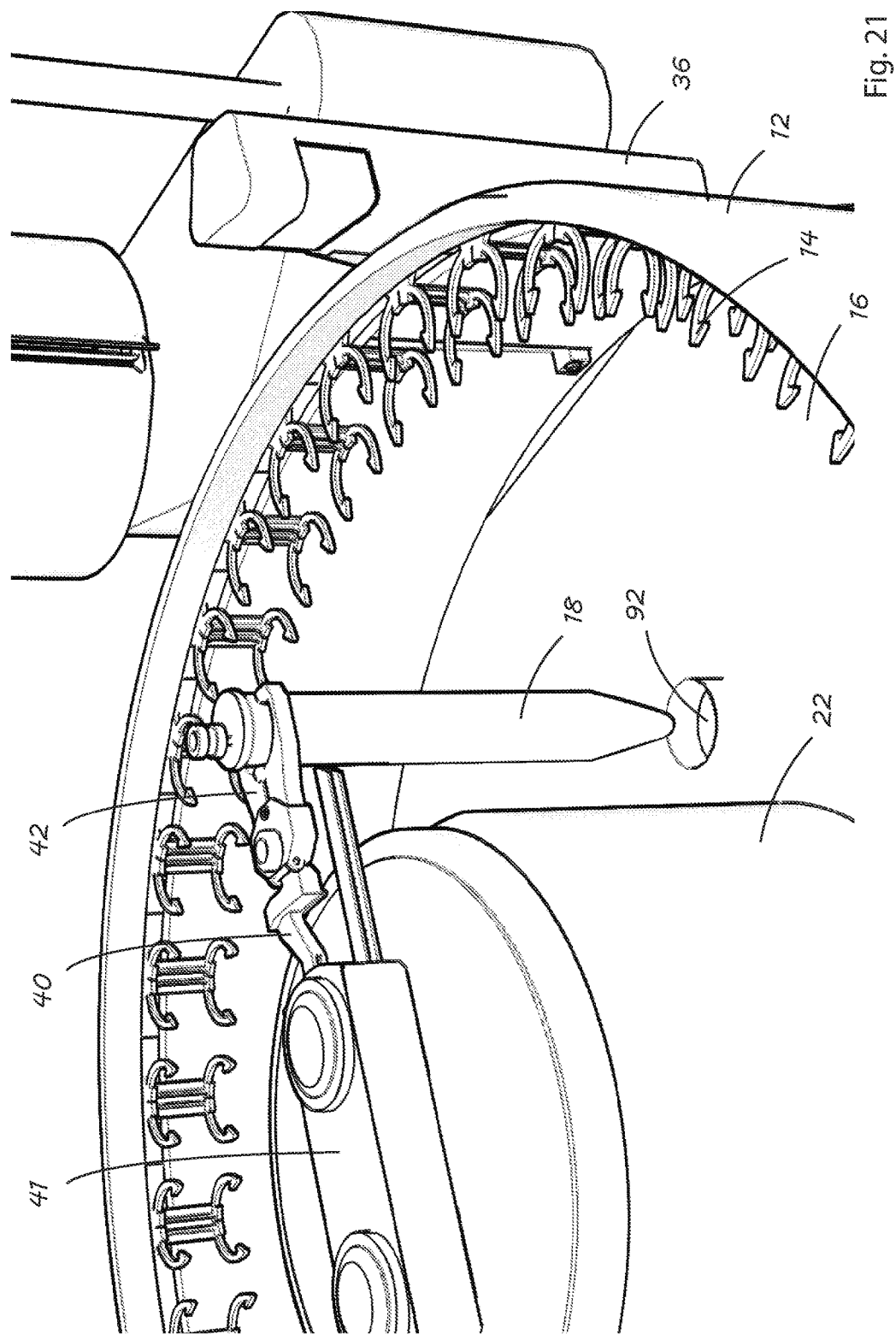

ARRANGEMENT FOR PREPARING A PLURALITY OF SAMPLES FOR AN ANALYTICAL METHOD

TECHNICAL FIELD

The invention relates to an assembly for sealing a vial present in a receptacle with a foil. The invention further relates to an assembly for taking up sample liquid from a vial and transferring the liquid to an analytic instrument, comprising a suction device and a needle or tube connected to said suction device.

The invention further relates to a sampling system for introducing samples provided on a sheet-like sample carrier into an empty or prepared vial with means for cutting the sheet-like sample carrier.

The invention further relates to an assembly for the preparation of a plurality of samples for an analytical method, comprising
(a) a carousel with a steady housing and moveable receptacles for sample vials;
(b) a control unit for controlling the receptacles in the carousel; and
(c) a sample taking device for providing the sample to the analytical method.

Samples, such as organic samples like blood, urine, serum, milk, honey and the like are examined in the laboratories regarding the presence of certain components or toxic substances and its quantities. Known methods of the instrumental analytics are used for this purpose, such as, for example, chromatographic, spectrometric or optical analytical methods. Normally the sample components which shall be examined are present in a sample matrix which can cause interferences. Some of the components must be changed, for example by changing the temperature, the pressure or the addition of reagents before they are accessible for the analytic method. The sample preparation is, therefore, an integral part of each instrumental analytical method.

An example for the analysis of blood is the screening of blood samples of newborn babies for the examination of hereditary diseases. With the DBS-Analysis (Dried Blood Spot-Analysis) samples are deposited in the form of a drop on a card of filter paper. For this purpose the sample carrier is provided with a marking. The sample dries on the sample carrier.

With instrumental analytical methods the analysis of samples itself is usually carried out automatically or semi-automatically. The sample is introduced in the measuring device and the device provides data representing either the kind and/or amount of the sample components which are examined or enable conclusions regarding the kind and/or amount by evaluating the data. Such data are, for example, chromatographic retention times, NMR-spectra, mass spectra, absorption- or emission spectra and the like.

While analytical measurements are carried out automatically or semi-automatically the sample preparation requires a multitude of chemical or physical steps which are normally carried out manually. Examples for such measures are cooling, heating, mixing, backflow-boiling, addition of reagents and solvents, separating of reagents by centrifugation or filtering, vortexing and the like.

Commonly, vials are closed with a plug. They are expensive.

PRIOR ART

Sample preparation devices are known in the prior art where a plurality of sample vials are accommodated in a common holder. A pipette with a dispensing system is arranged above the holder which is used to add a reagent. The holder can be handled as a whole, such as being transported or stored.

Autosamplers for graphite furnace atomic absorption spectroscopy are known where a plurality of readily prepared samples are provided in vials in a carousel. The carousel rotates whereby a selected sample can be positioned under a pipette which is used for sampling.

DE 20 2011 110 050 U1 discloses an assembly for examining dried samples on a carrier. The sample is extracted from the carrier and the extraction head used for this purpose is cleaned.

The enterprise PerkinElmer, Inc. sells products called "Panthera Puncher 9", which is an assembly for punching out a sample. The marked portion with the sample is cut out for the analysis and transferred into a vial together with the punched out portion of the sample carrier. Accordingly, the sample carrier forms an unwanted sample matrix. It is a disadvantage of the known methods that the cutting means used for punching is applied to different samples in a series which may cause contamination of the samples with sample particles of previous samples. Therefore, time consuming cleaning is required.

If the sample has not been deposited fully but only partly on the marked position on the sample carrier a manual adjustment is required or the sample is cut out only partly. This will cause a reduction of the sample mass whereby the detection limit is reduced.

It is disadvantageous with the sample preparation that each individual sample must be manually prepared even if semi-automatic methods carry out some of the steps simultaneously for several samples. In order to carry out a plurality of steps the sample is inserted into different vials. Solvents and reagents are added. With such proceedings the volume may change due to losses and there is the risk of contamination of the sample. Furthermore, the manual dosage is less accurate than an automatic dosage. Sample preparation is time consuming. The personnel concerned with sample preparation requires considerable special knowledge and becomes tired with progressing preparation time. The amount of samples which can be prepared in a laboratory for analysis is, therefore, limited.

DISCLOSURE OF THE INVENTION

It is an object of the invention to provide an assembly of the above mentioned kind which makes sample preparation simpler, quicker and increases the accuracy of the analytic results. It is another object of the invention with an assembly of the above mentioned kind to enable a high preparation rate for samples with little personnel requirements.

According to the invention this object is achieved with an assembly of the above mentioned kind, wherein
(c) a filter is provided inside the needle or tube;
(d) a depot with a plurality of unused needles or tubes is provided; and
(e) means are provided for exchanging the needle or tube after receiving sample liquid and introducing the sample in an analytic instrument for an unused needle or tube from the depot.

According to the invention the sample is not only taken, but also filtered. Solid particles can, of course, be removed from the sample with the centrifuge. However, remaining floating particles and microparticles can be filtered with the needle whereby the sample is introduced into the analytic instrument in a purely liquid state. This is particularly advantageous with HPLC. A cross-contamination by contaminated needles is avoided by using an unused needle from the depot.

The filter may at least partly be sintered by a sinter method. It may, however, also be provided that the tube or needle has a wall with reduced wall thickness in the range of the filter. In this case the filter may be provided with a filter material in the range of the wall with a reduced wall thickness and the opening there below may be closed by crimping. It is understood, however, that the opening underneath may also be designed differently which will keep the filter material in its position.

In a further modification of the invention optical means are provided for the detection of the depth of liquid supernatant above the solid state phase in the vial and means for controlling the insertion depth of the end provided at the sampling device according to the depth of the liquid supernatant. The optical means for the detection of the depth of liquid supernatant above the solid state phase in the vial may comprise a video camera with image processing means.

A reader can be provided for reading identification data and/or data for the required sample preparation from a bar code, RFID-storage or any other data storage provided at the sample or vial. Thereby, not only the identity of the sample is detected but also the method which should be used to prepare the sample. In such a way different kinds of samples in a more or less random order and different preparation methods can be introduced in the assembly or the carousel. Also, the same sample can be used with different sample preparation methods. The control knows the sample and the method at each point in time and can thereby optimize the path of the sample through the inventive assembly under consideration of the path of the other samples.

In a further embodiment of the invention an interface for connecting a HPLC-column, a gas chromatographic column or any other analytical instrument can be provided downline of the sampling device. In particular, a common control unit can be provided whereby the next sample can be readily prepared immediately after finishing an analysis and cleaning if required.

Preferably, furthermore an opening is provided in the carousel bottom in the range of the receptacle for vials provided at the centrifuge which is adapted to establish a connection to a waste container. In such a way the vial where the sample has been taken already can automatically be disposed of.

Furthermore, the object is achieved in that
(d) one or more stations are provided at the carousel for the sample preparation and receptacles for vials in the carousel can be positioned at such stations;
(e) a centrifuge having receptacles for vials which are positioned in pairs opposite to each other, and
(f) the receptacles for the vials are moveably fixed to the centrifuge and the movements are controllable in such a way that a transfer of a vial can be effected between a receptacle in the carousel and a receptacle in the centrifuge,
(g) wherein the control is effected with the same control unit which is used to control the carousel.

The receptacles for the vials can be arranged in a circle on the inside of the carousel and the centrifuge can be positioned in the center of the carousel. The receptacles for vials at the centrifuge can be formed by extendable gripping arms which are adjustable with respect to the rotational axis of the centrifuge. With such an assembly a sample preparation assembly is provided which is small, which can be produced at low costs and enables a fully automatic sample preparation. The individual preparation steps can be carried out at the stations for the sample preparation without having to transfer the sample to another vial in-between. The vials can be brought into any desired angular position with the gripping arms of the centrifuge. This means, that the vials can be moved from their position in the carousel to the next station with the gripping arms of the centrifuge independently of their actual position. If a station need not be used by a sample the sample my jump the queue and overtake the other samples. Thereby, the capacity utilization of the individual stations is improved, the sample preparation is accelerated and the preparation rate is increased. The double use of a centrifuge as a sample preparation station and simultaneously as a means for positioning enables treating selected samples with higher priority. This is particularly useful with perishable samples which should be analyzed as fast as possible.

The vials are inserted into the receptacles in the carousel of the assembly according to the present invention. This can be effected with or without a sample therein. The sample may also be inserted into the vial after insertion into a receptacle. The sample will exit the vial only for the analysis thereafter and remains in the same vial for the entire sample preparation.

Afterwards the samples are moved along the various stations in the carousel. For this purpose the carousel moves in the housing.

With a preferred embodiment of the invention a sampling system is provided for introducing the sample into an empty or prepared vial in the carousel. The sampling system thereby forms a first station for sample preparation.

The sample can be inserted in the form of solid matter or as a liquid.

Furthermore, it is an object of the invention to provide an assembly for sealing a vial present in a receptacle of the carousel with a foil from a foil dispenser. The device may comprise:
(a) means for placing foil from a foil dispenser above the vial;
(b) a male form movably arranged in the range above the vial; and
(c) a heating for heating the male form in the range of the upper edge of the vial in such a way that the foil is welded to the edge upon pressing the male form onto the edge;
(d) wherein the male form exerts a pressure on the vial when the vial is sealed.

During the welding a portion of the foil in the opening range of the vial is released from the remaining foil. The foil need not, therefore, be adapted to the size and form of the opening. It is sufficient if the foil is available in the form of sheets or in large pieces.

Preferably, the foil dispenser is provided with a reel carrying the foil. Much foil can be provided with such an embodiment. The change of the reel is relatively simple. The foil can be unrolled in the desired way.

A Vortex-mixer is preferably provided below the male form and the vial is movable in the range between the male form and the Vortex mixer. It can be provided that the vial is pressed on the Vortex-mixer with the male form. At this station, therefore, the foil is welded on and the vial is pressed on the Vortex-mixer simultaneously. It is understood, however, that the foil may also be welded on without mixing or the pressure of the male form may also be exerted without the foil.

Furthermore, means are provided for expelling solvent from a vial in a receptacle in the carousel by means of a gas.

In particular, the solvent can be expelled with two hollow tubes which are pushed through the foil in the vial. One tube is used to introduce a neutral gas, such as nitrogen, into the vial. The second tube is used to suck out solvent-containing gas.

Finally, it is an object of the invention to provide an assembly of the above mentioned kind which facilitates the transfer of samples on sheet-like sample carriers into a vial and avoids contamination.

There are samples, which are present in the form of dried blood drops or the like on a sheet-like carrier. Such samples can be stamped out or cut out with the carrier and are then dropped into the vial.

According to the invention this object is achieved with a sampling system for introducing samples from a sheet-like sample carrier into an empty or prepared vial with means for cutting the sheet-like sample carrier of the above mentioned kind, by
(a) a jet nozzle;
(b) a high pressure fluid source connected to the jet nozzle; and
(c) means for controlling the movement of the jet nozzle and/or the sample carrier in such a way that selected portions of the sheet-like sample carrier is cut out.

With such an assembly the carrier is cut out with a high pressure jet beam. A cutting blade is not necessary. Thereby, cross-over contamination from sample to sample at the cutting blade is avoided. The high pressure fluid may comprise at least one fluid used in the sample preparation method. This has the advantage that no unnecessary liquids are used which must be removed in the later course of the sample preparation which involves some effort.

The portion of the sample carrier with the sample can be fully cut out and transferred into the vial. Alternatively, the portion of the sample carrier with the sample is cut out only partly and means are provided for swinging down the cut out portion in the range of the vial and means for flushing the sample from the sample carrier with the fluid from the high pressure fluid source into the vial. A matrix generated by the sample carrier is thereby avoided. In particular, the means for flushing the sample can comprise a spraying head for spraying the fluid from the high pressure fluid source onto the sample. Thereby, the pressure of the fluid need not be reduced.

In a particularly preferred embodiment of the invention a scanner is provided for scanning the color, the degree of dryness, the position of the sample, the extent of the sample and/or further optically detectable features of the sample. The sample carrier and the jet nozzle with the high pressure beam can be moved alone or both in such a way that the sample is exactly cut out. The sample carrier can be moved under a fixed jet nozzle. The entire holder of the sample carrier can be mounted on an x-y-table for this purpose. The movement is controlled by the control unit. Alternatively, the jet nozzle is moved. It is also possible to move both components. In order to detect the kind and the degree of dryness of the sample, an image of the sample can be taken with several different wavelengths of the spectrum. Thereby, it is avoided that undesired samples enter the analytic system. The same camera can be used to detect identification data, such as a bar code.

With the sampling and placing the sample on the carrier it is not always easy to exactly hit the location which is cut out. Such placing tolerances can be taken into account when cutting with a controlled movement. The entire sample enters the vial. It is understood, however, that also only a portion of the sample can be cut out and flushed into the vial on purpose if, for example, the remains shall be used for further analysis or as a reference.

Preferably, a housing tower is provided adapted to hold a stack of sample carriers separated with distance pieces and means for moving a sample carrier from an opening in the housing tower to the range under the jet nozzle. The opening in the housing tower can be provided at the lower end and the housing tower can have an upper opening for refilling further sample carriers.

As a further stop, one or more dispenser systems may be provided for adding reagents for the sample preparation from a reservoir, wherein the dispensing exit of the dispenser system is fixed above the vials moving in the carousel in such a way that the reagent can be individually introduced into selected vials. Normally, such dispenser systems comprise a pump dispensing a desired volume of the reagents. The pump can be individually controlled by the control. Such reagents may be precipitants, solvents, matrix modifiers, contrast reagents and the like.

In a further modification of the invention a heating is provided for heating one or more vials in the carousel.

The assembly operates fully automatically and does not require personnel with specific knowledge in the field of the art. It is only necessary to provide the samples in a suitable manner. The individual steps and methods are stored beforehand and carried out by the control unit.

Further modifications of the invention are subject matter of the subclaims. An embodiment of the invention is described below in greater detail with reference to the accompanying drawings.

BRIEF DESCRIPTION OF THE DRAWINGS

FIG. 9 is a perspective view of a foil dispenser in an assembly of FIG. 1 for sealing a vial present in a receptacle in the carousel with foil.

FIG. 10 is a cross sectional view of the foil dispenser of FIG. 9.

FIG. 11 shows a heating in the assembly of FIG. 1.

FIG. 12 shows the heating of FIG. 11 during heating procedure.

FIG. 13 shows a sample-taking device of the assembly of FIG. 1.

FIG. 14 is a cross sectional view of a hollow needle with a filter for taking a sample.

FIG. 15 shows a camera for determining the height of the liquid supernatant in the vial in a first position.

FIG. 16 shows the camera of FIG. 15 in a second position.

FIG. 17 shows the rotating valve of the sample taking device for an assembly of FIG. 1 in a first position.

FIG. 18 shows the rotating valve of the sample taking device for an assembly of FIG. 1 in a second position.

FIG. 20 illustrates how the needle and the vial are disposed of after taking the sample.

FIG. 21 illustrates the disposal of the vial after sample taking in the bottom of the housing.

DESCRIPTION OF AN EMBODIMENT

Figure 1:
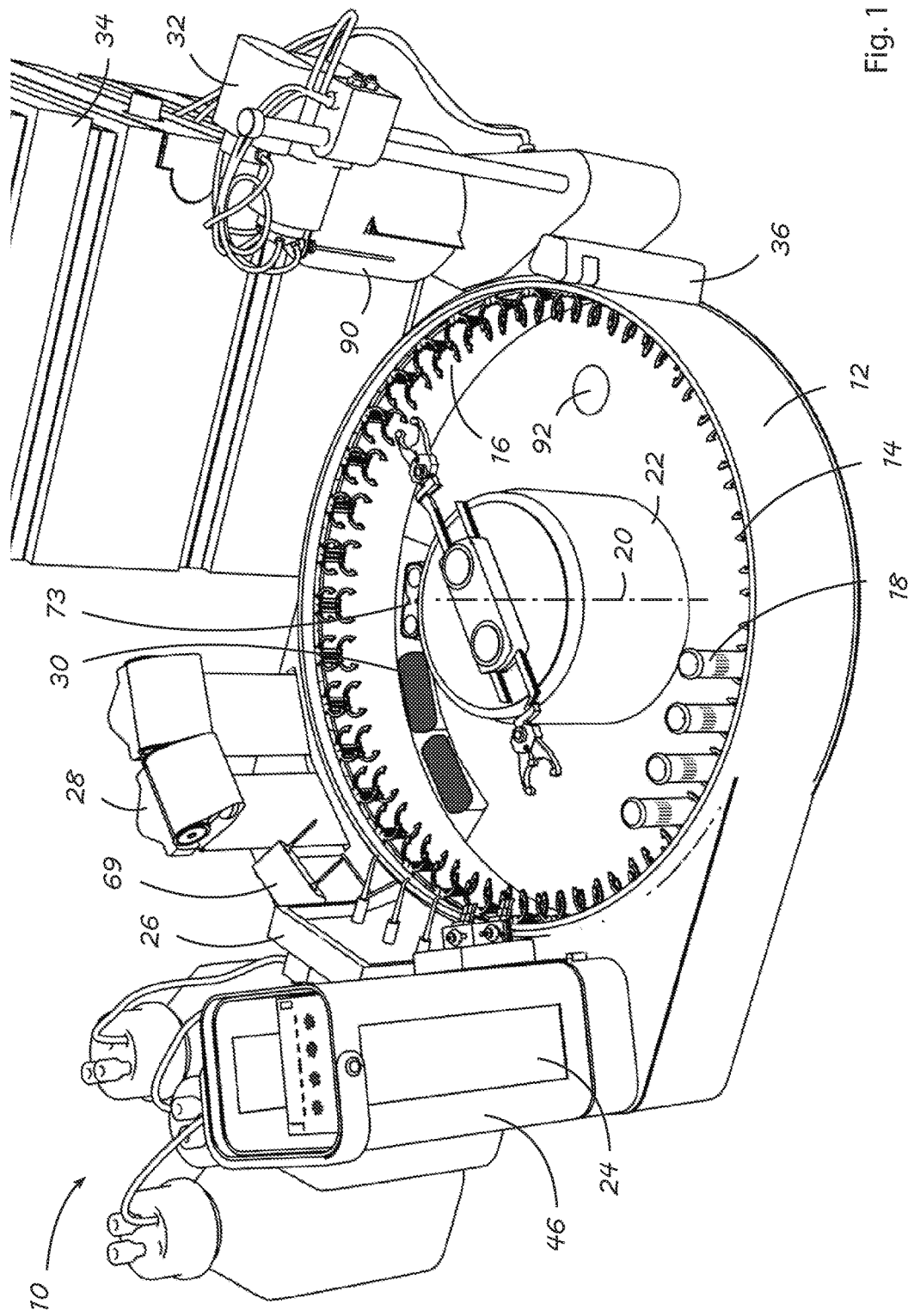
FIG. 1 is a perspective view of an assembly for sample preparation with several stations and a centrifuge.

FIG. 1 shows an assembly for the preparation of samples generally designated with numeral 10. The assembly is provided with an essentially circular housing 12 with a carousel 14. The carousel 14 consists of a ring with a plurality of receptacles 16 for sample containers or vials 18. The vials 18 can be clipped in a radial direction into openings in the receptacles 16 provided for this purpose. Alternatively the vials 18 can be inserted from above into the receptacles 16. The carousel 14 can be rotated about a center axis 20. An actuator and a control unit 34 are provided for this purpose which are not shown here in order to keep the illustration simple.

A centrifuge 22 is arranged in the center portion of the carousel. The centrifuge 22 also rotates about the center axis 20. Various stations for sample preparation are provided outside along the housing, including a station for sample introduction and sample taking. A sampling system 24 for introducing dried samples from a sheet-like carrier is one of said stations. The next station in a clockwise direction has three dispensing systems 26 for dispensing reagents for sample preparation from a reservoir. The next station 28 in a clockwise direction is a foil dispenser for sealing a vial 18 present in a receptacle 16 in the carousel 14 with a foil. A Vortex-station 30 is positioned below the foil dispenser 28. The Vortex-station 30 can be well seen in FIGS. 9 and 10.

A sample taking device 32 is positioned on the side opposite to the sampling system 24. The taken samples which are readily prepared are transferred to an analytic instrument, which is a HPLC-column with a detector (not shown) in the present embodiment.

All stations and devices described above are connected to a common control unit (not shown). The control unit controls all required drivers and actuators and receives and stores data and results. Settings can be either directly made at the station or with a user-interface at the control unit. Sample preparation methods with kind and duration of the individual sample preparation steps can be inserted and stored.

Figure 2:
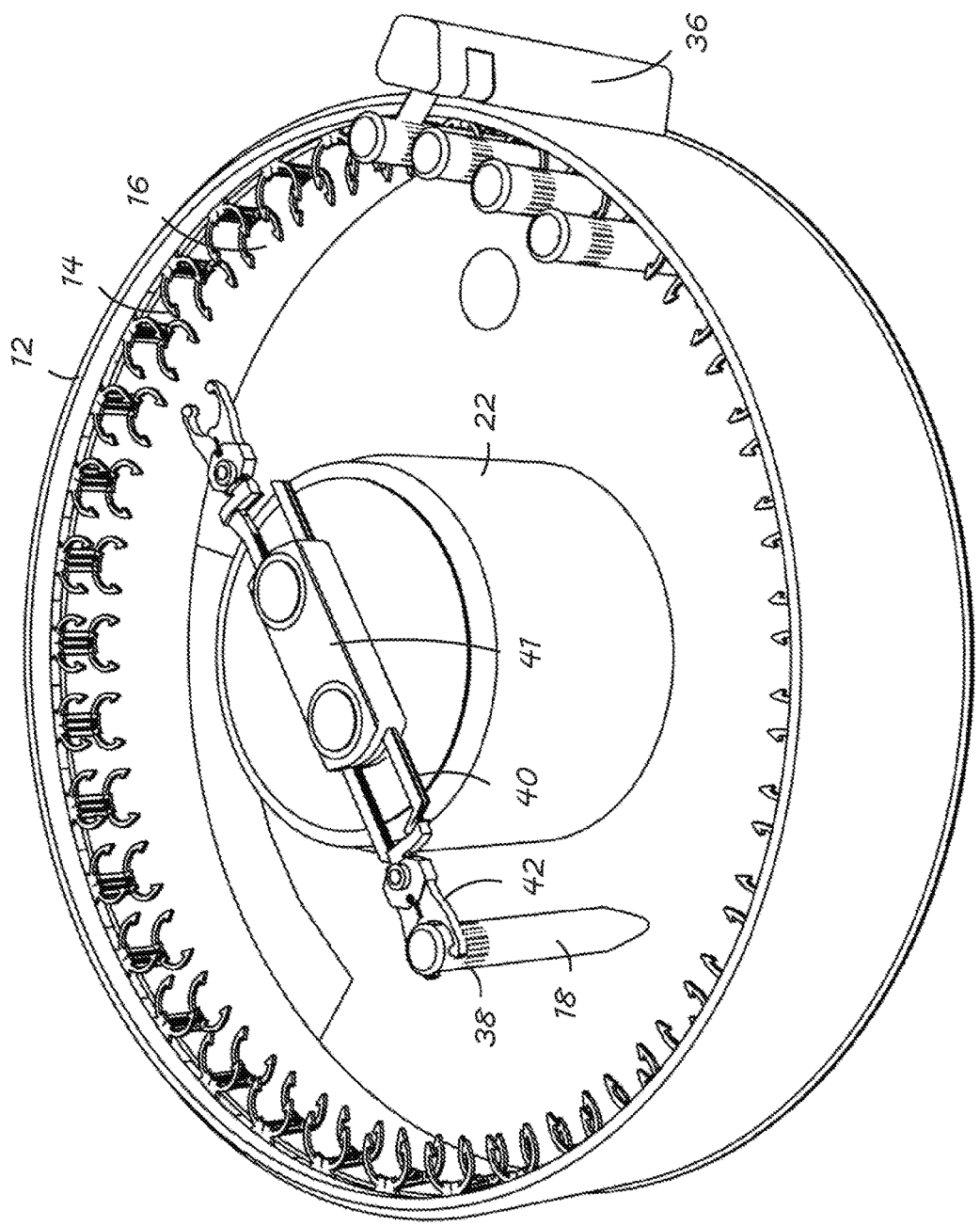
FIG. 2 is a perspective view of the sample carousel and the centrifuge in an idle state as used in the assembly of FIG. 1.

FIG. 2 shows the housing 12 in greater detail. The housing 12 has a transparent cover (not shown) for closing in order to avoid contamination of the samples. Furthermore, the environmental air is protected of evaporating solvents and the like.

The vials 18 are held in the receptacles 16. Each vial 18 has the form of a test-tube and is provided with a bar code 38, which is stuck to the vial 18 in the form of a printed sticker. On the outside, the housing 12 has an ordinary barcode scanner 36. The scanner 36 serves as a reader and reads the data stored in the barcode. In the present embodiment such data comprise an identification number. The identification number relates to the kind of sample, such as blood or urine, and a specific sample preparation method. The scanner 36 transfers the position, i.e., the angular position of the receptacle 16 in the carousel 14 and the identification number to the control unit. The control unit determines the required sample preparation steps using such identification number and moves the vial to the individual stations.

The samples in the vials 18 can move along the stations in the order of their positions. However, there are cases where some stations need not be used, where a station is occupied or where a sample shall be treated with higher priority. For this purpose the vial can be shifted with gripping arms 40 of the centrifuge 22 to another receptacle 16. For this purpose the gripping arms 40 are adapted to be moved in a radial direction. They are extended from a holder 41 which rotates together with the actuator. They can be extended as far as the carousel. A pliers-shaped gripper 42 is provided at the end of the gripping arms 40 which is adapted to grip the vial 18 and hold it. Suitable actuators with sliding contacts for power supply are provided for each gripping arm 40 and each gripper 42. By slowly rotating the centrifuge 22 a vial 18 can be moved from one receptacle to another receptacle 16.

Figure 3:
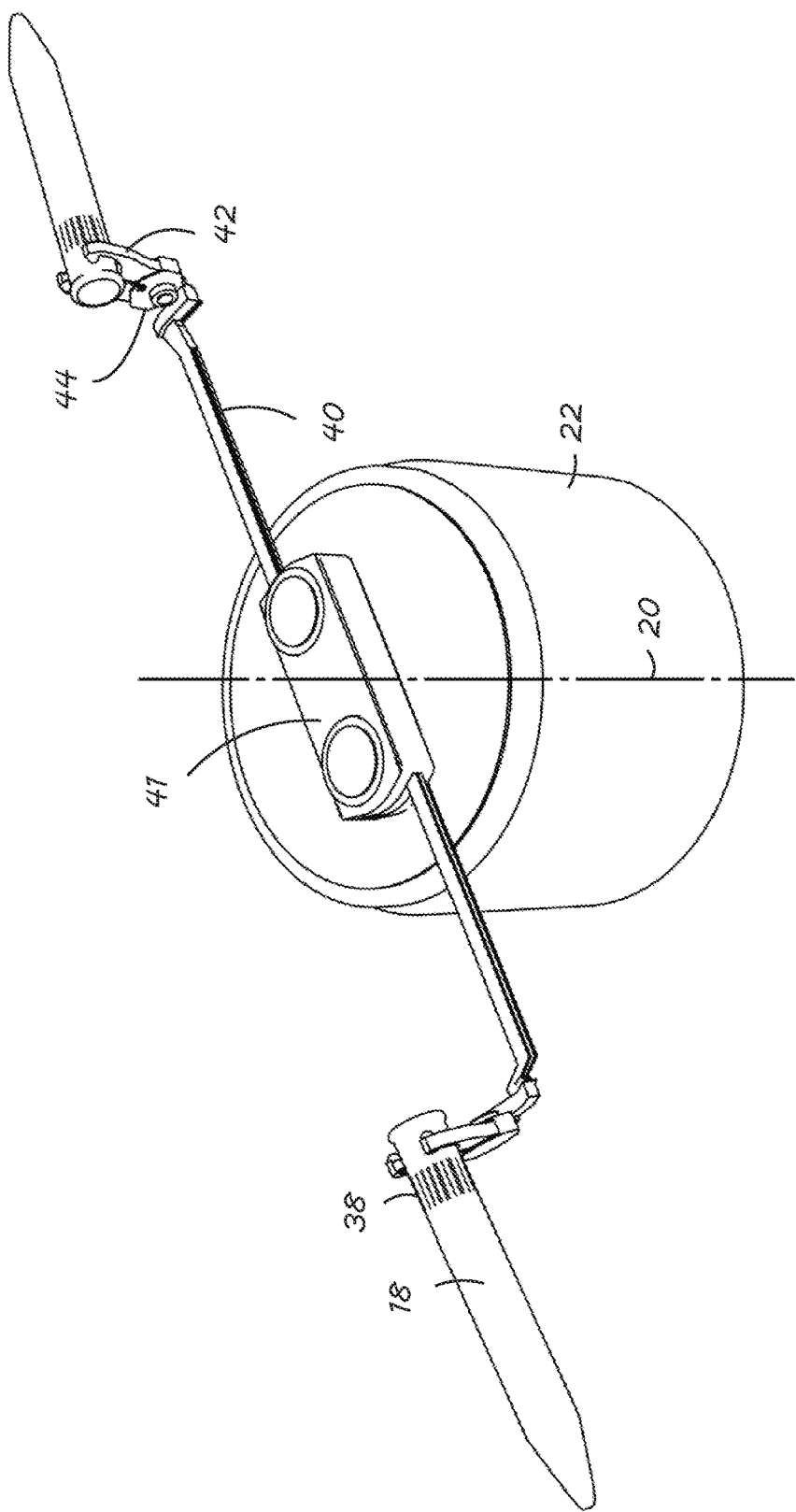
FIG. 3 shows the centrifuge of the assembly in FIGS. 1 and 2 during the centrifugation in greater detail.

In the present embodiment two gripping arms 40 are shown at the centrifuge 22. However, it is also possible to provide several pairs of opposite gripping arms 40. In any case the centrifuge 22 has a double function: first, samples can be exposed to centrifugation as with common centrifuges. This is shown in FIG. 3. Second, the centrifuge 22 can be accurately controlled and serves to move a vial from one receptacle 16 to another. During centrifugation the centrifuge rotates very quickly. Centrifugal forces are generated and the solid particles in the sample are moved outwards to the bottom of the vial. The grippers 42 are hinged to the gripping arms 40. In such a way the vial 18 can be positioned in an almost horizontal position during centrifugation. This is shown in FIG. 3.

Figure 4:
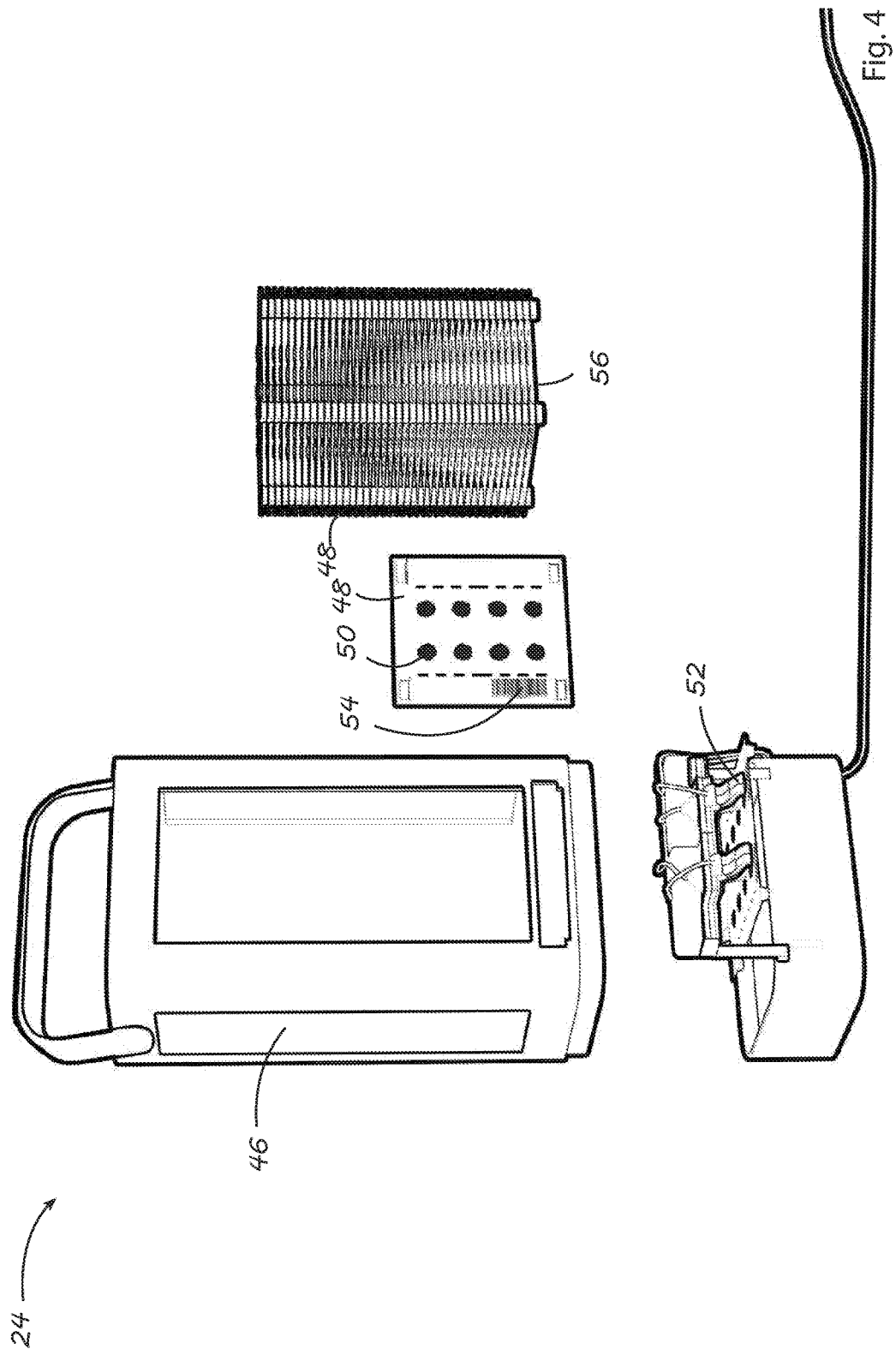
FIG. 4 shows the entire sampling system for dried samples on a sheet-type carrier.
Figure 5:
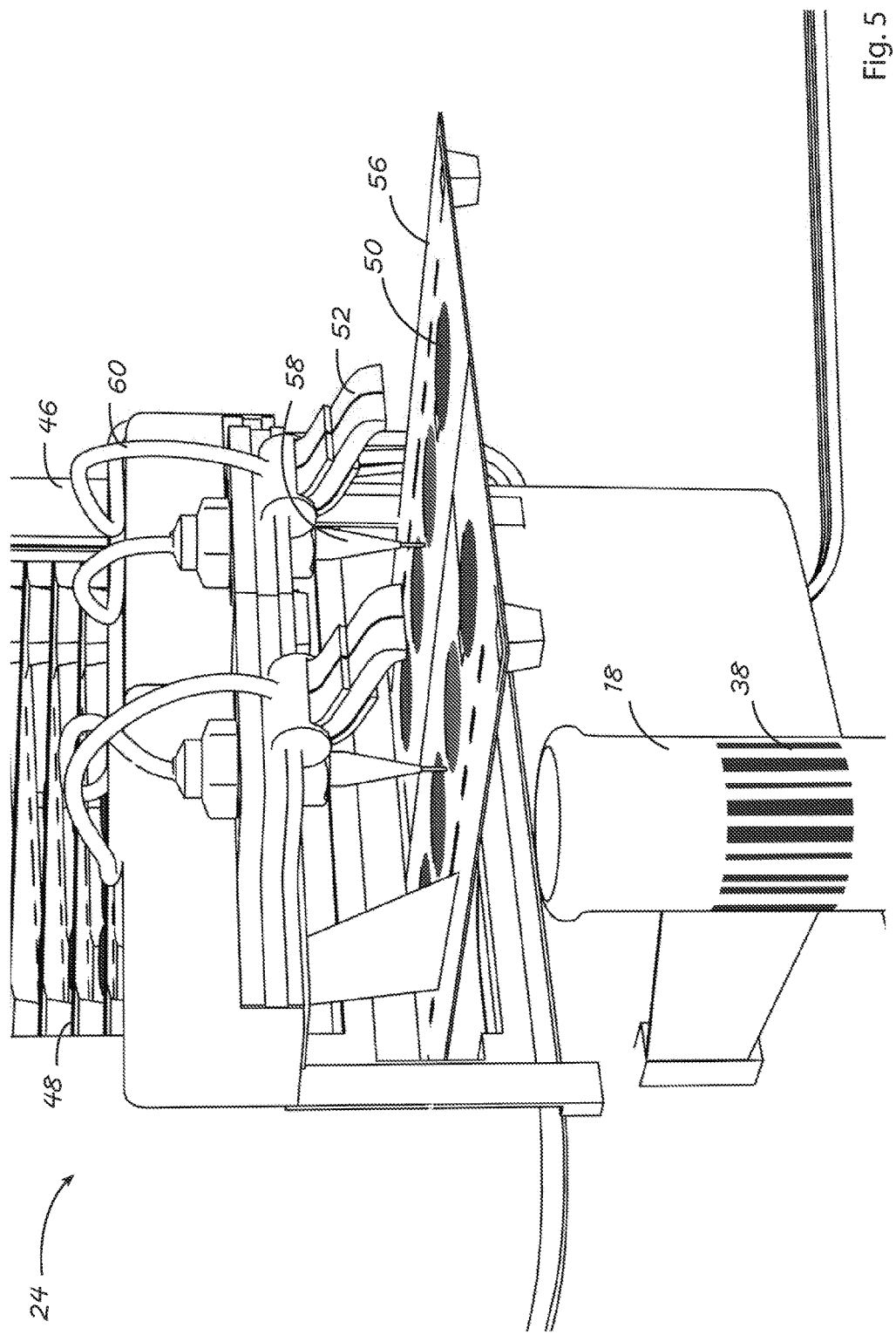
FIG. 5 shows the sampling system of the assembly in FIG. 4 in greater detail.

FIG. 4 and FIG. 5 show the sampling system 24. The sampling system 24 for introducing samples comprises a removable and exchangeable housing 46. The housing 46 forms a tower where sheet-like sample carriers 48 can be stored in a stack. Distance pieces are provided between the sample carriers. Dried samples 50 are present on the sample carriers 48. An example for such a dried sample is a dried drop of blood. The samples are present in well-defined positions which are marked so that the sample can be directly positioned on this position during sample taking.

Each sample carrier 48 is provided with a bar code 54. The bar code 54 is read by a common bar code scanner 52 or a camera. The data are transmitted to the control unit for tracking. If there are several samples, several bar codes may be provided. The same scanner 52 is used to determine the exact position of the samples 50 on the sample carrier. The scanner 52 operates with different wavelengths of the optical spectrum and can thereby also detect the kind of sample. Samples with an undesired or unknown appearance can be excluded from the sampling in order to avoid contamination of the assembly. It is also possible to determine the position with a further scanner or to use a pre-set position.

The lowest sample carrier 56 is moved in the range above a vial 18. A suitable actuator (not shown) is provided for this purpose. The actuator is an x-y-actuator and the holder for the sample carriers is mounted thereon. The actuator enables, therefore, not only a horizontal movement of the sample carrier 56 in a direction perpendicular to the housing 46 but also in a lateral horizontal direction which is parallel to the front end of the housing wall.

A high pressure jet nozzle 58 is held at the front housing wall of the housing 46. This is shown in FIG. 5. The high pressure jet nozzle 58 is connected to a solvent reservoir with a high pressure pipe 60. A high pressure jet beam can be generated with a pump (not shown). The high pressure jet beam exits the high pressure jet nozzle 58 in the direction of the sample carrier 56. The high pressure jet beam is conditioned in such a way that the sample carrier 56 is cut. With a suitable movement of the sample carrier 56 the portion under the high pressure jet nozzle 58 is cut out. The control of the movement is effected with the common control unit. In the present embodiment the sample 56 is cut out only partly. The sample 50 is then flushed down with solvent from the sample carrier 56 into the vial 18. A spray head is provided for flushing which is also operated with high pressure fluid. Alternatively, the entire portion of the sample carrier 56 is cut out and the sample 50 falls into the vial 18 together with the portion of the sample carrier 56 which carries the sample.

The solvent is a solvent which is used anyway in the further proceedings of sample preparation. Therefore, it need not necessarily removed from the vial which would involve a certain effort.

Depending on the application and the kind of sample carrier, several samples may be cut out simultaneously. In the present embodiment two adjacent samples 50 are cut out with two adjacent high pressure jet beams. For this purpose two high pressure jet nozzles 58 are provided in the housing 46.

In an alternative embodiment which is not shown here, the high pressure jet nozzle is moved instead of the sample carrier 56. However, the same result is obtained at all times.

Figure 6:
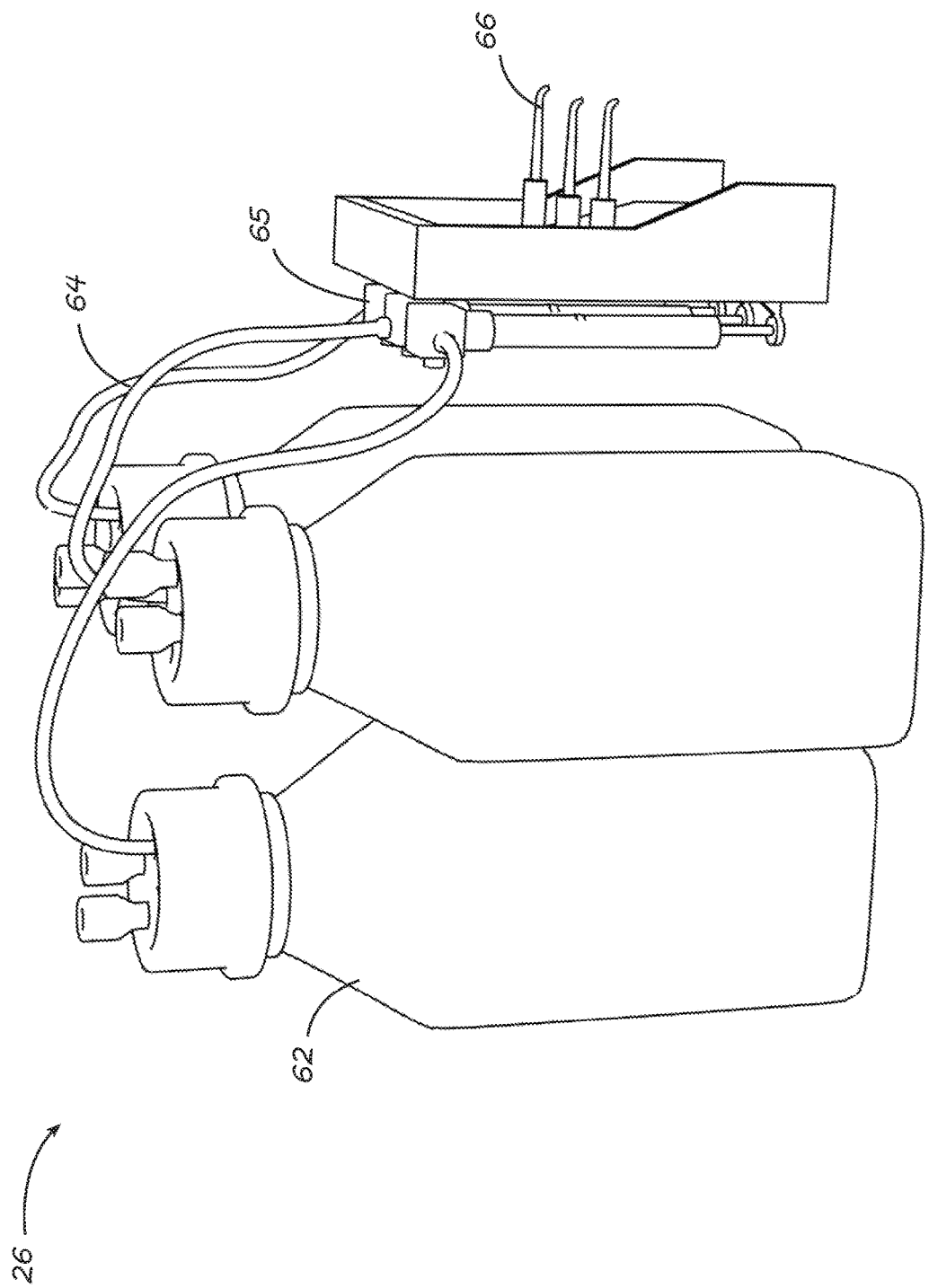
FIG. 6 shows three dispenser systems of an assembly of FIG. 1 for dispensing reagents from a reservoir for the sample preparation.

FIG. 6 shows three dispenser systems 26 for dispensing reagents for the sample preparation from a reservoir 62. An example for a reagent is a precipitation agent for precipitation of interfering portions of the sample matrix. Solvents and diluting agents can also be added if this is good for the analysis. The reagent is present in a reservoir 62. Each of the three reservoirs 62 is connected to a dosing pump by a tube connection 64. The dosing pump is controlled by the control unit. The reagent from the reservoir 62 is dispensed with a well-defined volume from the reservoir 62 to the dispensing nozzle and into the vial 18 there below. The three dispensing nozzles can be seen in FIG. 6.

In the present embodiment three dispensing systems 26 are provided which can operate simultaneously. In such a way the same reagent can be dispensed into three vials at the same time. Thereby, a high dispensing rate is achieved. Depending on the application, however, it is also possible to use different reagents for different applications or sample preparation methods.

Figure 7:
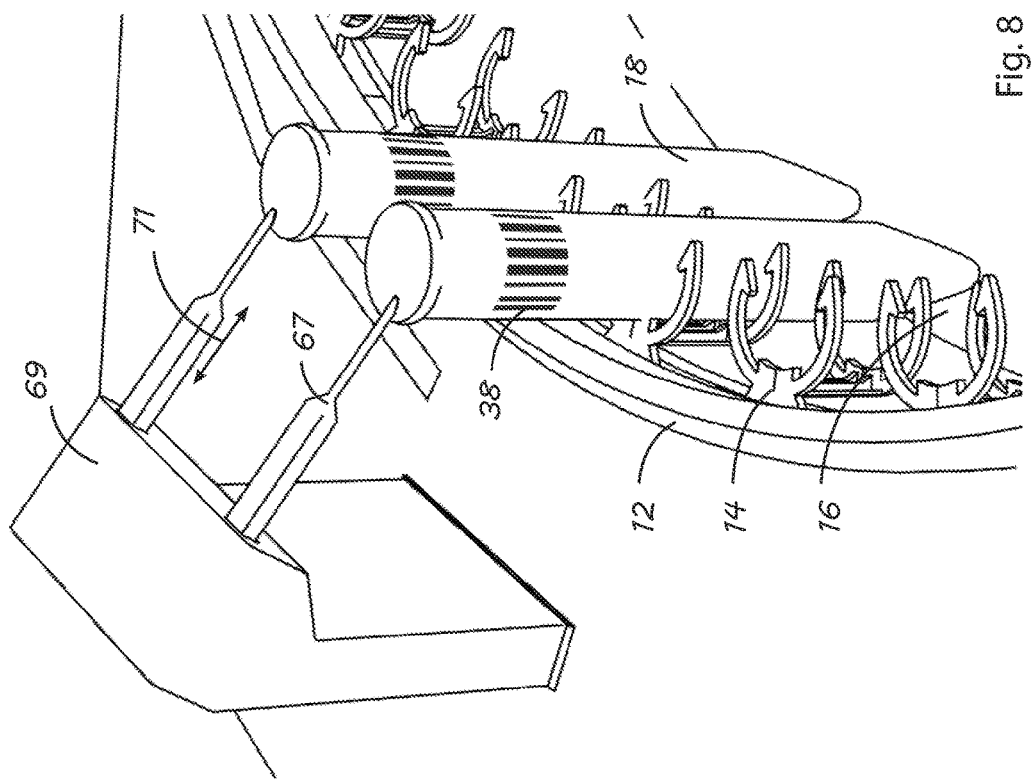
FIG. 7 shows the expelling device for expelling of solvents in an assembly of FIG. 1 in an idle position.
Figure 8:
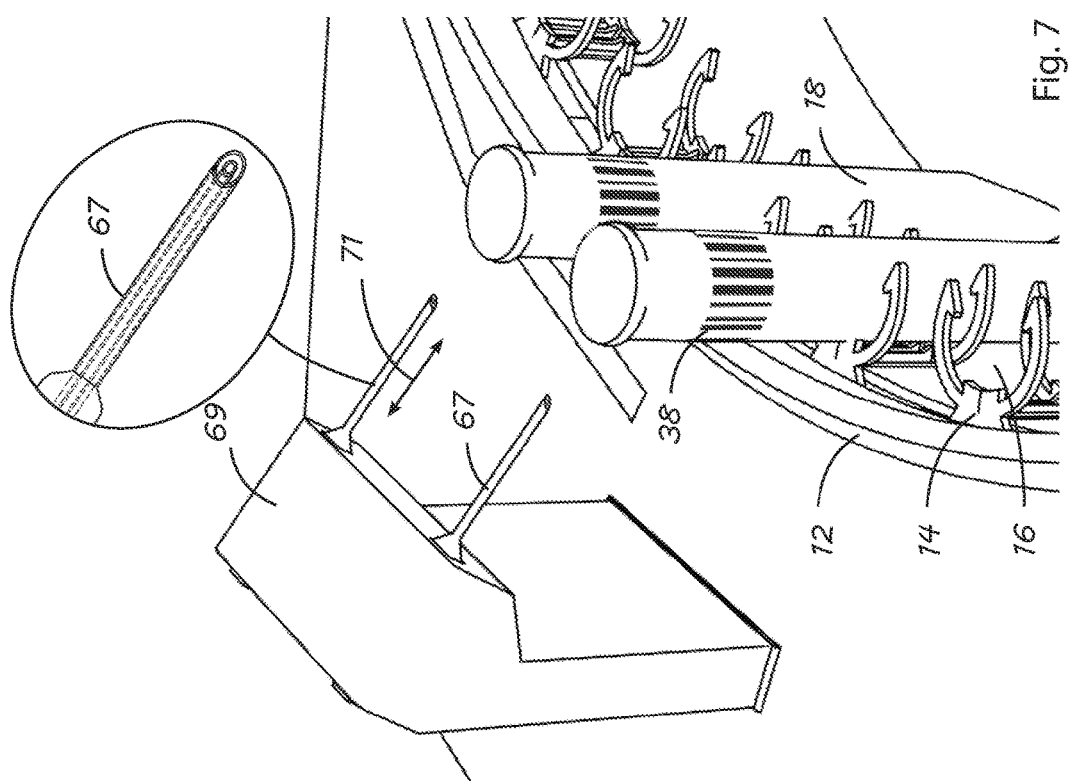
FIG. 8 shows the expelling device of FIG. 7 in operating position.

FIGS. 7 and 8 illustrate how unwanted solvent is removed from the sample. A neutral gas, which is pressurized nitrogen gas in the present embodiment, is inserted by means of a tube 67 into the vial. Solvent present in the sample is released and removed to the outside through another tube. The tubes 67 are moveable from an idle position as shown in FIG. 7 to an operating position which is shown in FIG. 8. The moving direction is indicated by an arrow 71. A suitable actuator is provided in the holder 69. In the present embodiment two tubes or needles 67 are provided for removing solvent. The nitrogen gas supply tube is moved from the outer periphery of the carousel towards the farer diameter of the tube sealed as described below in such a way that it punches the seal. A second tube which is used as the fume exit is linked to the supply tube. Nitrogen will be supplied and flows down the test tube walls forming a cyclone. The nitrogen evaporates the solvent or reagent.

FIG. 9 and FIG. 10 show two foil dispensers 28 for sealing a vial present in a receptacle in the carousel with a foil 68. FIG. 10 is a cross section through the foil dispenser 28. The foil 68 is unrolled from a foil reel 70 above the vial 18. The foil reel 70 is held in a holder 72. The holder 72 is provided with an arm 74 radially extending in a forward direction. The foil 68 is guided downwards over the arm 74 and a deflection roller 76. Thereby, the foil 68 is stretched in a horizontal direction between a male form 78 and the upper edge 80 of the vial 18. The male form 78 has essentially the same diameters as the upper edge 80 of the vial 18. The upper edge 80 of the vial is rounded in order to provide tearing of the foil. A heating (not shown) is provided inside the male form 78 which is controlled by the control unit. The heating is formed by a coiled glow filament in a cartridge.

For sealing the vial 18 a section of unused foil is unrolled. A reel 82 with an actuator (not shown) is provided at the lower end of the foil for this purpose. The unused foil is placed between the male form 78 and the edge 80. The holder 72 is then moved downwards with the arm 74 and the heated male form 78 connected thereto. For this purpose an actuator (not shown) is provided. The actuator is controlled by the control unit. Due to the pressure and the increased temperature, the foil is welded to the edge. The foil in the range of the vial is released from the remaining foil 68. The vial 18 is tightly sealed. The welding is carried out in a way which avoids the entering of fumes into the vial.

Depending on the application the vial 18 can be further pressed down. Vortex-station 30 is positioned below the vial 18 and the male form 78. Upon exerting a pressure on the vial 18 the Vortex-movement is carried out. The sample in the vial 18 is mixed (vortexed).

Depending on the desired sampling rate, a plurality of foil dispensers 28 can be arranged in a series. In this case several vials 18 can be sealed simultaneously. Alternatively, only a plurality of male forms is used which seal several vials 18 simultaneously using a wider foil. In the present embodiment two foil dispensers 28 are used with two foils (see FIGS. 1 and 9).

A heating 73 is provided next to the Vortex-Station 30. This is shown in FIG. 11. The heating 73 has a housing with two receptacles 75. The heating 73 is adapted to be moved in a vertical direction. For this purpose an actuator (not shown) controlled by the control unit is provided. The housing of the heating 73 is moved upwards. Thereby the receptacles 75 surround the lower range of the vials 18 provided above and can heat them. This situation is shown in FIG. 12.

For separating solid particles, two of the vials 18 are gripped with opposite gripping arms 40 of the centrifuge 22 and rotated.

A sample taking device 32 is provided for taking a sample and transferring it to the analytic instrument. This is shown in FIG. 13. The sample taking device 32 comprises a hollow needle 84 at a moveable conical head 86. The head 86 is fixed to a pole and can be moved upwards and downwards. A suitable actuator (not shown) is provided for this purpose, which is controlled by the control unit. For taking the sample the vial 18 is moved below the hollow needle 84. The hollow needle 84 is then moved downwards until it enters into the sample. The entering depth is controlled by a vertically moveable video camera with image processing whereby it is achieved that the entering depth is independent of the height of the solid portion always half of the liquid height. FIG. 15 shows the video camera in a lower position. FIG. 16 shows the video camera in an upper position.

Filter material 88 is present in the hollow needle 84. This can be seen in FIG. 14. In a first embodiment (shown on the left hand side in the representation) the filter material is simply inserted into the needle. In a second alternative embodiment (represented in the middle of the illustration) the filter is sintered at the bottom of the needle material, such as polymer or metal. In a third alternative embodiment the needle 88 is bored from below whereby a region with a lower wall thickness is obtained. The filter material is inserted in this range and the lower portion of the needle is closed by crimping.

If sample liquid is sucked into the hollow needle 84 solid particles and floating particles are held back in the filter material 88. A piston pump 114 is provided for this purpose. The sample prepared in such a way can be directly introduced in a HPLC column or any other analytical instrument.

A fresh needle with unused filter material is used for each sample. They are stored in a depot 90 with an ejector. Therefore, the used needle is released before a new sample can be taken and a fresh needle is fixed to the head.

Figure 19:
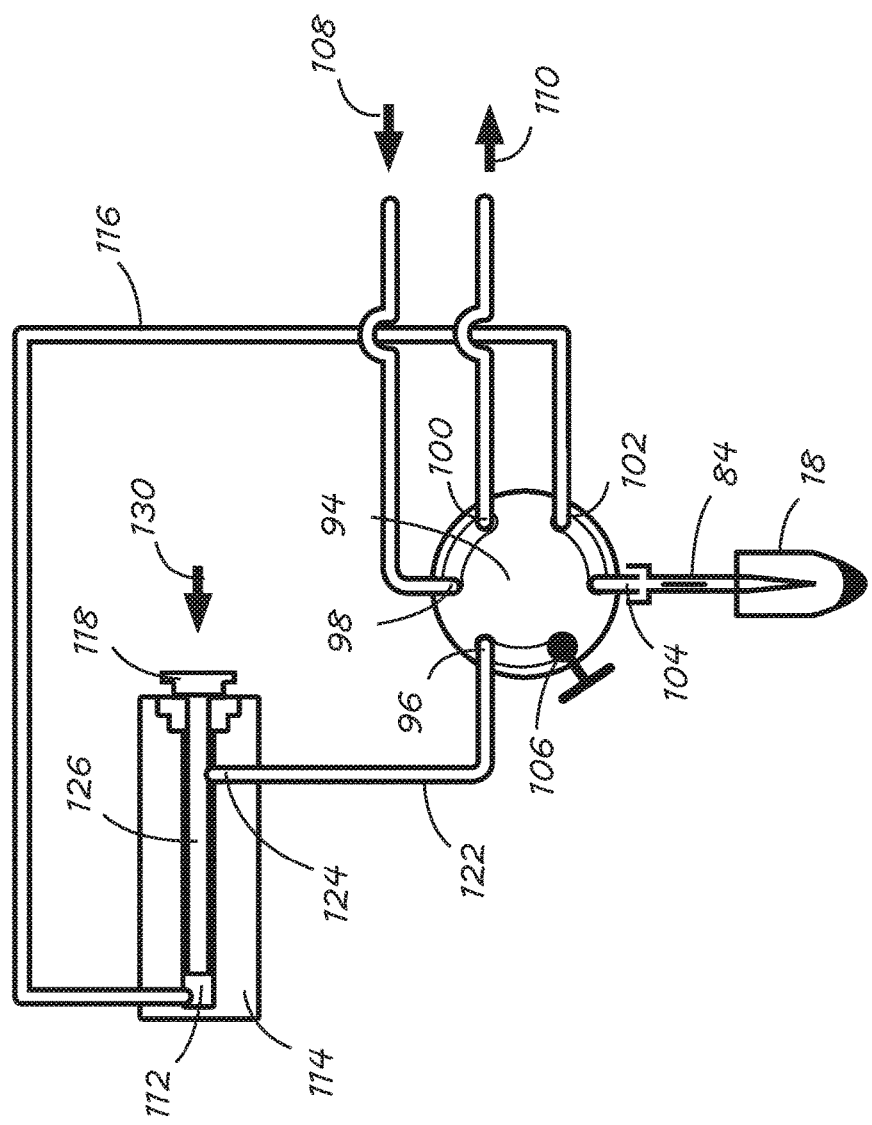
FIG. 19 shows the rotating valve of the sample taking device for an assembly of FIG. 1 in a third position for flushing.

The sample from the vial 10 is transferred to the analytical instrument with the sample taking device 32. In the present embodiment a chromatographic column (not shown) is used for the analysis. A rotary valve 94 having 6 ports 96, 98, 100, 102, 104 and 106 is used for this purpose. A measuring device, a pump and a filter needle is connected to the rotary valve. This is shown in FIGS. 17 to 19.

Eluent from an eluent source is added at port 98. This is represented by an arrow 108. Port 100 is connected to a chromatographic column. In the present embodiment a HPLC column, not shown, is used. This is represented by an arrow 110. Port 102 is connected to the port 112 of a piston system 114 through pipe 116. The piston system 114 is operated with a stepper motor 118. This is represented by an arrow 120. Port 96 is connected to a second port 124 of the piston system 114 through pipe 122.

FIG. 17 shows a valve position where the needle 84 enters the sample liquid present in the vial 18. In this position eluent is pumped into the HPLC column. The piston 126 of the piston system 114 is moved in the direction of arrow 120 with the stepper motor 118.

A well-defined volume of sample liquid 128 is sucked through the needle 84 to the port 104 and through the port 102 to the pipe 116 which has the form of a loop. Dead volume of the needle and the valve are well considered therein.

The valve is then moved to the position shown in FIG. 18. The sample present in the loop is then connected to the exit to the HPLC column through port 102 and port 100. If the piston is moved to the left in the representation the sample is pumped into the HPLC column. Simultaneously, eluent flows through port 98 to port 96 and through pipe 122 to the piston system 114.

For flushing, the valve is rotated back as shown in FIG. 19. The piston 126 is moved in the direction of the arrow 130. Eluent present in the system is pushed through pipe 116 and ports 102 and 104 to the needle 84. Leftover sample portions are released and flushed out into the vial 18. In this position eluent also flows through ports 98 and 100 to the HPLC column whereby the column is also flushed.

After sample taking and flushing of the valve, the needle 84 is released and dropped into the vial and the vial 18 is gripped with the gripping arm 40 of the centrifuge 22 and transferred to an opening 92 in the bottom of the housing 12 by opening the grippers 42 above the opening 92. This is illustrated in FIG. 21. A waste container is provided below the opening 92 receiving used vials 18 with flushing liquid. Simultaneously, a new needle is acquired.

By moving the piston to the right in the representation the next sample can be sucked up and the cycle can be repeated.

The control unit is provided in a housing together with a power supply and the required electronic components, for example next to or under the housing 12. The housing is well aired and shielded against chemicals and vapors. With the control unit samples of higher priority can be treated more quickly during sample preparation even if the system is already occupied with different samples. A sensor can identify idle positions, count them and report them to the control unit. When inserting the vials the user can enter the amount of needed positions with the accompanying priority. They are then adequately considered by the control unit. Samples with contents which cannot be analyzed by the system in the present configuration will be returned without any treatment. In such a way excessive contamination is avoided.

Temperatures in the male form 78 and in the heating, the rotational speed and the angle at the centrifuge, the dispensing volumes and the kind and order of the sample preparation can be adjusted with the control unit. The control unit also processes and displays signals of sensors, cameras and scanners.

The invention claimed is:

1. An assembly for the preparation of a plurality of samples for an analytical method, comprising
    a carousel with an inside, a center, and a steady housing;
    carousel receptacles for sample vials arranged in a circle on said inside of said carousel and configured to be moved along said circle;
    a sample taking device for providing a sample;
    one or more stations at said carousel for sample preparation wherein said carousel receptacles are configured to be moved by a carousel movement and positioned at said one or more stations;
    a centrifuge positioned in said center of said carousel and having a rotational axis;
    centrifuge receptacles for said vials moveably fixed to said centrifuge and positioned in pairs opposite to each other wherein said centrifuge receptacles are formed by extendable gripping arms which are adjustable with respect to said rotational axis of said centrifuge for moving said centrifuge receptacles in a centrifuge movement; and
    a control unit for controlling said carousel and centrifuge movement and movement of said vials in any of said receptacles for transferring a vial between carousel receptacle and a centrifuge receptacle using the extendable gripping arms.

2. The assembly of claim 1, and further comprising a sampling system for introducing said sample into an empty or prepared vial in said carousel.

3. The assembly of claim 2, and wherein said sampling system comprises an assembly for transferring samples provided on a sheet-like sample carrier into an empty or prepared vial with means for cutting said sheet-like sample carrier, and further comprising
    a jet nozzle, the jet nozzle and/or said sheet-like sample carrier configured to carry out a movement;
    a high pressure fluid source connected to said jet nozzle the high pressure fluid source configured to eject high pressure fluid from said jet nozzle; and
    means for controlling said movement in such a way that selected portions of said sheet-like sample carrier can be cut out.

4. The assembly of claim 3, and wherein said high pressure fluid comprises at least one fluid used in said sample preparation method.

5. The assembly of claim 3, and wherein said portion of said sample carrier with said sample is cut out entirely and transferred into said vial.

6. The assembly of claim 3, and wherein said portion of said sample carrier with said sample is cut out only partly and means are provided for swinging down said cut out portion in said range of said vial and means are provided for flushing said sample from said sample carrier with said fluid from said high pressure fluid source into said vial.

7. The assembly of claim 3, and wherein said sample has a color, a degree of dryness, a position, and extent and wherein a scanner is provided for scanning said color, said degree of dryness, said position of said sample, said extent of said sample and/or further optically detectable features of said sample.

8. The assembly of claim 1, and further comprising one or more dispenser systems with a dispensing exit for adding reagents for said sample preparation from a reservoir, wherein said dispensing exit is fixed above said vials moving in said carousel whereby said reagent can be individually introduced into selected vials.

9. The assembly of claim 1, and further comprising a device for sealing a vial present in a receptacle in said carousel with a foil from a foil dispenser.

10. The assembly of claim 9, and further comprising a foil dispenser with foil and means for placing said foil from said foil dispenser above said vial;
a male form movably arranged above said vial; and
a heating means for heating said male form in a range of said upper edge of said vial in such a way that said foil is welded to said edge upon pressing said male form onto said edge;
wherein said male form exerts a pressure on said vial when said vial is sealed.

11. The assembly of claim 1, and wherein one station is formed by a male form and a Vortex-mixer below said vial and said vial is configured to be pressed on said Vortex-mixer with said male form movably arranged above said vial.

12. The assembly of claim 10, and wherein a Vortex-mixer is provided below said vial and said vial with said receptacle is configured to be moved between said male form and said Vortex-mixer.

13. The assembly of claim 1, and wherein a heating means for heating one or more vials is provided in said carousel.

14. The assembly of claim 1, and wherein means are provided for expelling solvent from a vial in a receptacle in said carousel by means of a gas.

15. The assembly of claim 1, and wherein said sample taking device for providing said sample for said analytic method comprises:
a suction device; and
a needle or tube connected to said suction device;
a filter inside said needle or tube;
a depot with a plurality of unused needles or tubes; and
means for exchanging said needle or tube after receiving said sample liquid and introducing said sample liquid in an analytic instrument by an unused needle or tube from said depot.

16. The assembly of claim 1, and wherein said sample liquid is present in said vial with a liquid supernatant with a depth above a solid state phase and a needle provided at said sampling device is configured to be inserted into said sample liquid with an end of said needle and the assembly further comprising optical means for the detection of said depth of said liquid supernatant and means for controlling said insertion depth of said end of said needle of said depth of said liquid supernatant.

17. The assembly of claim 1, and further comprising a reader at said carousel for reading identification data and/or data for said required sample preparation from a bar code, RFID-storage or any other data storage provided at said sample or vial.

18. The assembly of claim 1, and wherein an interface for connecting a HPLC-column, a gas chromatographic column or any other analytical instrument is provided downline said sampling device.

19. The assembly of claim 18, and wherein the carousal has a bottom and an opening is provided in the range of said receptacles for vials provided at said centrifuge in said bottom of said carousel which connects said carousel to a waste container.

* * * * *